United States Patent
Smith

(10) Patent No.: US 8,398,240 B2
(45) Date of Patent: Mar. 19, 2013

(54) SINGLE-FIBER MULTI-SPOT LASER PROBE FOR OPHTHALMIC ENDOILLUMINATION

(75) Inventor: Ronald T. Smith, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 180 days.

(21) Appl. No.: 12/917,911

(22) Filed: Nov. 2, 2010

(65) Prior Publication Data

US 2011/0122366 A1    May 26, 2011

Related U.S. Application Data

(60) Provisional application No. 61/263,957, filed on Nov. 24, 2009.

(51) Int. Cl.
- *A61B 3/10* (2006.01)
- *A61B 19/00* (2006.01)
- *A61B 18/18* (2006.01)
- *A61N 5/06* (2006.01)

(52) U.S. Cl. .......... 351/221; 351/205; 607/88; 128/898; 606/4

(58) Field of Classification Search .................. 351/221, 351/200, 246, 205, 218, 213–215; 607/88–94; 128/898; 606/1–18
See application file for complete search history.

(56) References Cited

U.S. PATENT DOCUMENTS

| | | | |
|---|---|---|---|
| 3,584,948 A | 6/1971 | Herriott | |
| 4,062,043 A | 12/1977 | Zeidler et al. | |
| 4,111,524 A | 9/1978 | Tomlinson, III | |
| 4,274,706 A | 6/1981 | Tangonan | |
| 4,679,901 A | 7/1987 | Dammann et al. | |
| 4,865,029 A | 9/1989 | Pankratov et al. | |
| 4,986,262 A | 1/1991 | Saito | |
| 5,090,400 A | 2/1992 | Saito | |
| 5,125,922 A | 6/1992 | Dwyer et al. | |
| 5,150,254 A | 9/1992 | Saitou | |
| 5,261,904 A | 11/1993 | Baker et al. | |
| 5,275,593 A | 1/1994 | Easley et al. | |
| 5,356,407 A | 10/1994 | Easley et al. | |
| 5,373,526 A | 12/1994 | Lam et al. | |
| 5,396,571 A | 3/1995 | Saadatmanesh et al. | |
| 5,409,137 A | 4/1995 | Bonomelli | |
| 5,555,129 A | 9/1996 | Konno et al. | |
| 5,630,809 A | 5/1997 | Connor | |
| 5,659,642 A | 8/1997 | King et al. | |
| 5,715,089 A | 2/1998 | Shiraishi | |
| 5,841,912 A | 11/1998 | Mueller-Fiedler et al. | |
| 5,921,981 A | 7/1999 | Bahmanyar et al. | |
| 5,973,779 A | 10/1999 | Ansari et al. | |

(Continued)

FOREIGN PATENT DOCUMENTS

| | | |
|---|---|---|
| EP | 1191359 A1 | 3/2002 |
| WO | 99/08612 A1 | 2/1999 |

(Continued)

*Primary Examiner* — Dawayne A Pinkney

(57) ABSTRACT

An ophthalmic endoilluminator is provided. The ophthalmic endoilluminator includes a light source, a first optical assembly, an optical coupling element, and an optical fiber having an optical grating located distally on the optical fiber, the optical fiber optically coupled to the optical coupling element. The first optical assembly receives and substantially collimates the white light. The optical coupling element receives the substantially collimated white light from the first optical assembly and directs the light to an optical fiber. The optical grating couples to the distal end of the optical fiber, the optical grating having a surface relief grating, and an overlayer optically coupled to the surface relief grating. The optical grating is operable to substantially diffract incident light into N diffraction orders, the N diffraction orders having a substantially uniform intensity.

16 Claims, 13 Drawing Sheets

U.S. PATENT DOCUMENTS

| | | | |
|---|---|---|---|
| 5,980,454 | A | 11/1999 | Broome |
| 6,066,128 | A | 5/2000 | Bahmanyar et al. |
| 6,071,748 | A | 6/2000 | Modlin et al. |
| 6,080,143 | A | 6/2000 | Connor |
| 6,096,028 | A | 8/2000 | Bahmanyar et al. |
| 6,097,025 | A | 8/2000 | Modlin et al. |
| 6,241,721 | B1 | 6/2001 | Cozean et al. |
| 6,370,422 | B1 | 4/2002 | Richards-Kortum et al. |
| 6,421,179 | B1 | 7/2002 | Gutin et al. |
| 6,441,934 | B1 | 8/2002 | Boord et al. |
| 6,520,956 | B1 | 2/2003 | Huang |
| 6,539,132 | B2 | 3/2003 | Ivtsenkov et al. |
| 6,562,466 | B2 | 5/2003 | Jiang et al. |
| 6,563,982 | B1 | 5/2003 | Xie et al. |
| 6,687,010 | B1 | 2/2004 | Horii et al. |
| 6,975,898 | B2 | 12/2005 | Seibel |
| 7,071,460 | B2 | 7/2006 | Rush |
| 7,231,243 | B2 | 6/2007 | Tearney et al. |
| 7,252,662 | B2 | 8/2007 | McArdle et al. |
| 7,566,173 | B2 | 7/2009 | Auld et al. |
| 2001/0055462 | A1 | 12/2001 | Seibel |
| 2002/0013572 | A1 | 1/2002 | Berlin |
| 2002/0054725 | A1 | 5/2002 | Ivtsenkov et al. |
| 2002/0111608 | A1 | 8/2002 | Baerveldt et al. |
| 2003/0020922 | A1 | 1/2003 | Crowley et al. |
| 2003/0081220 | A1 | 5/2003 | Ostrovsky et al. |
| 2004/0012856 | A1 | 1/2004 | Gutin |
| 2004/0109164 | A1 | 6/2004 | Horii et al. |
| 2004/0116909 | A1 | 6/2004 | Neuberger et al. |
| 2004/0195511 | A1 | 10/2004 | Elmore et al. |
| 2005/0075704 | A1 | 4/2005 | Tu et al. |
| 2005/0140033 | A1* | 6/2005 | Jiang et al. .................... 264/1.7 |
| 2005/0143719 | A1 | 6/2005 | Sink |
| 2005/0154379 | A1 | 7/2005 | McGowan, Sr. et al. |
| 2005/0197655 | A1 | 9/2005 | Telfair et al. |
| 2005/0240168 | A1 | 10/2005 | Neuberger et al. |
| 2005/0245916 | A1 | 11/2005 | Connor |
| 2006/0013533 | A1 | 1/2006 | Slatkine |
| 2006/0100613 | A1 | 5/2006 | McArdle et al. |
| 2006/0106370 | A1 | 5/2006 | Baerveldt et al. |
| 2006/0114473 | A1 | 6/2006 | Tearney et al. |
| 2006/0195076 | A1 | 8/2006 | Blumenkranz et al. |
| 2007/0057211 | A1 | 3/2007 | Bahlman et al. |
| 2007/0121069 | A1 | 5/2007 | Andersen et al. |
| 2007/0179430 | A1 | 8/2007 | Smith et al. |
| 2007/0238955 | A1 | 10/2007 | Tearney et al. |
| 2007/0265602 | A1 | 11/2007 | Mordaunt et al. |
| 2007/0296094 | A1 | 12/2007 | Jiang et al. |
| 2007/0299430 | A1 | 12/2007 | McArdle et al. |
| 2008/0013960 | A1 | 1/2008 | Tearney et al. |
| 2008/0097225 | A1 | 4/2008 | Tearney et al. |
| 2008/0246919 | A1 | 10/2008 | Smith |
| 2008/0308730 | A1 | 12/2008 | Vizi et al. |

FOREIGN PATENT DOCUMENTS

WO      2006/116141 A1      11/2006

* cited by examiner

SINGLE-FIBER MULTI-SPOT LASER PROBE FOR OPHTHALMIC ENDOILLUMINATION

This application claims priority to U.S. Provisional Application Ser. No. 61/263,957 filed on Nov. 24, 2009.

TECHNICAL FIELD OF THE INVENTION

The present disclosure relates to an illuminator for use in ophthalmic surgery and more particularly to an ophthalmic endoilluminator to produce a light suitable for illuminating the inside of an eye.

BACKGROUND OF THE INVENTION

Anatomically, the eye is divided into two distinct parts—the anterior segment and the posterior segment. The anterior segment includes the lens and extends from the outermost layer of the cornea (the corneal endothelium) to the posterior of the lens capsule. The posterior segment includes the portion of the eye behind the lens capsule. The posterior segment extends from the anterior hyaloid face to the retina, with which the posterior hyaloid face of the vitreous body is in direct contact. The posterior segment is much larger than the anterior segment.

The posterior segment includes the vitreous body—a clear, colorless, gel-like substance. It makes up approximately two-thirds of the eye's volume, giving it form and shape before birth. It is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free-flowing like the aqueous humor and has normal anatomic attachment sites. One of these sites is the vitreous base, which is a 3-4 mm wide band that overlies the ora serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, such as vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions are made on the sclera at the pars plana. The surgeon inserts microsurgical instruments through the incisions such as a fiber optic light source to illuminate inside the eye, an infusion line to maintain the eye's shape during surgery, and instruments to cut and remove the vitreous body.

During such surgical procedures, proper illumination of the inside of the eye is important. Typically, a thin optical fiber is inserted into the eye to provide the illumination. A light source, such as a metal halide lamp, a halogen lamp, a xenon lamp, or a mercury vapor lamp, is often used to produce the light carried by the optical fiber into the eye. The light passes through several optical elements (typically lenses, mirrors, and attenuators) and is launched at the optical fiber that carries the light into the eye. The quality of this light is dependent on several factors, including the types of optical elements selected.

Techniques that are commonly used to illuminate the inside of the eye are brightfield imaging, darkfield imaging, and gradient field imaging. Gradient field imaging is created by illuminating a feature by partially overlapping an illumination spot so that parts of the feature are well lit by direct illumination and parts of the feature are dim or back-lit by scattered light, or through dynamic contrast by moving an illumination beam over the retinal feature. Because endoscopic illumination is provided by inserting a probe tip through a small incision, the fact that the probe may have to be articulated through the incision point, and that the illumination probe is at a finite angel of incidence relative to a viewing microscope, providing desirable contrast is difficult to realize in a practical surgical setting.

Patterned (structured) illumination can be used to provide contrast by which a surgeon can visualize ocular structures, such as retinal structures. To obtain desirable contrast illumination, it is preferable to create a regular pattern of illumination (irregular illumination patterns, such as spiral ring patterns or donut patterns, do not provide favorable contrast). However, illuminator probes that can efficiently provide structured illumination safe for use in ophthalmic procedures are unknown.

SUMMARY OF THE INVENTION

The present disclosure provides an ophthalmic endoilluminator that substantially eliminates or reduces disadvantages and problems associated with previously developed systems. More specifically, the present disclosure provides an ophthalmic endoilluminator light source that fiber-couples to an ophthalmic endoilluminator fiber to illuminate interior regions of the eye. In one embodiment, the ophthalmic endoilluminator includes a light source, a first optical assembly, an optical coupling element, and an optical fiber having an optical grating located distally on the optical fiber, the optical fiber optically coupled to the optical coupling element. The first optical assembly receives and substantially collimates the white light. The optical coupling element then receives the substantially collimated white light from the first optical assembly and directs the light to an optical fiber. The optical grating couples to the distal end of the optical fiber, the optical grating having a surface relief grating, and an overlayer optically coupled to the surface relief grating. The optical grating is operable to substantially diffract incident light into N diffraction orders, the N diffraction orders having a substantially uniform intensity.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

DESCRIPTION OF THE INVENTION

Preferred embodiments of the present disclosure are illustrated in the FIGS., like numerals being used to refer to like and corresponding parts of the various drawings.

Embodiments of the present disclosure substantially address problems associated with illuminating the interior of the eye. More specifically, an ophthalmic endoilluminator is provided that includes a light source, a first optical assembly, an optical coupling element, and an optical fiber having an optical grating located distally on the optical fiber, the optical fiber optically coupled to the optical coupling element. The first optical assembly receives and substantially collimates the white light. The optical coupling element then receives the substantially collimated white light from the first optical assembly and directs the light to an optical fiber. The optical grating couples to the distal end of the optical fiber, the optical grating having a surface relief grating, and an overlayer optically coupled to the surface relief grating. The optical grating is operable to substantially diffract incident light into N diffraction orders, the N diffraction orders having a substantially uniform intensity. The optical fiber/optical grating conducts the light into an interior region of the eye.

Figure 1:
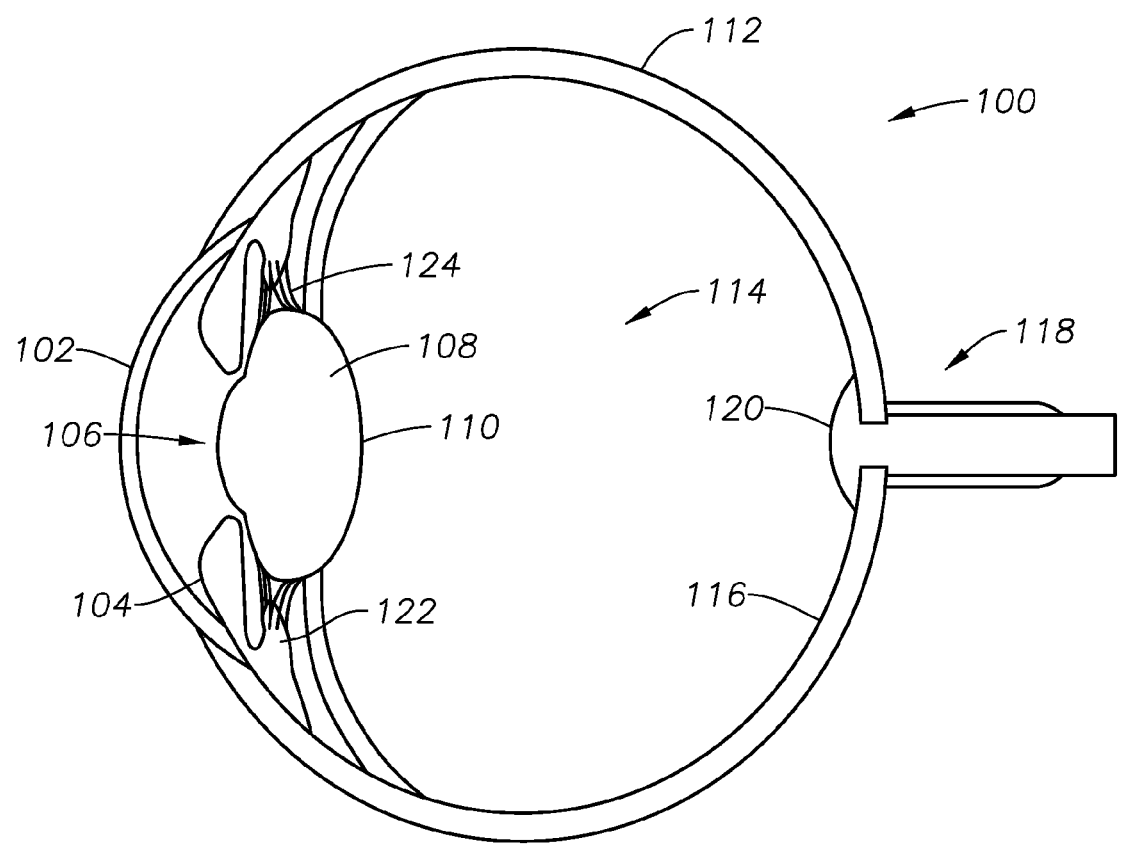
FIG. 1 illustrates the anatomy of the eye in which an ophthalmic endoilluminator in accordance with embodiments of the present disclosure may be placed.

FIG. 1 illustrates the anatomy of the eye into which the improved design for ocular implant provided by the present disclosure may be placed. Eye 100 includes cornea 102, iris 104, pupil 106, lens 108, lens capsule 110, zonules 124, ciliary body 122, sclera 112, vitreous gel 114, retina 116, macula 120, and optic nerve 118. Cornea 102 is a clear, dome-shaped structure on the surface of the eye that acts as a window, letting light into the eye. Iris 104 is the colored part of the eye, a muscle surrounding the pupil 106 that relaxes and contracts to control the amount of light entering the eye. Pupil 106 is the round, central opening of the iris 104. Lens 108 is a structure inside the eye that primarily helps to focus light on the retina 116. Lens capsule 110 is an elastic bag that envelops the lens 108, helping to control lens shape when the eye focuses on objects at different distances. Zonules 124 are slender ligaments that attach the lens capsule 110 to the inside of the eye, holding the lens 108 in place. The ciliary body 122 is the muscular area attached to the lens 108 that contracts and relaxes to control the size of the lens 108 for focusing. Sclera 112 is the tough, outermost layer of the eye that maintains the shape of the eye. Vitreous gel 114 fills the large section of the eye that is located towards the back of the eyeball and helps to maintain the curvature of the eye. Retina 116 is a light-sensitive nerve layer in the back of the eye that receives light and converts it into signals to send to the brain. The macula 120 is the area in the back of the eye that contains functions for seeing fine detail. Optic nerve 118 connects and transmits signals from the eye to the brain.

Ciliary body 122 lies just behind the iris 104. Attached to the ciliary body 122 are tiny fiber "guide wires" called zonules 124. Lens 108 is suspended inside the eye by the zonular fibers 124. Nourishment for the ciliary body 122 comes from blood vessels which also supply the iris 104. One function of ciliary body 122 is to control accommodation by changing the shape of the lens 108. When the ciliary body 122 contracts, the zonules 124 relax. This allows the lens 108 to thicken, increasing the eye's ability to focus up close. When looking at a distant object, ciliary body 122 relaxes, causing the zonules 124 to contract. The lens 108 then becomes thinner, adjusting the eye's focus for distance vision.

Ophthalmic endoilluminators have been previously based either on halogen tungsten lamps or high pressure arc lamps (metal-halides, Xe). The advantages of arc lamps are a small emitting area (<1 mm), color temperature close to daylight, and longer life than in halogen lamps—e.g., about 400 hours vs. about 50 hours. The disadvantage of arc lamps is high cost, decline in power, complexity of the systems and the need to exchange lamps several times over the life of the system.

An LED based illuminator provided by embodiments of the present disclosure may provide considerably lower cost and complexity, and characteristic life times of 50,000 to 100,000 hours that would allow operating an ophthalmic fiber illuminator for the entire life of the instrument with very little drop in output and without a need of exchanging LEDs.

Light from a typical white LED is generated by using ultra violet (UV)/Violet/Blue light to excite a white phosphor cap that emits white light. Currently all white LEDs could be considered spatially extended sources of illumination (3 mm diameter or so phosphor areas) with high numerical aperture. Thus, current white LEDs are not well suited for coupling into a single optical fiber. Available pig-tailed fiber illuminators based on white LEDs use fiber butted against an LED phosphor. In these illuminators, only a small fraction of the emitted light can be coupled into a low numerical aperture and small diameter optical fiber. Therefore, available pig-tailed white LED sources deliver low levels of light. Embodiments of the present disclosure generate additional white light optical signals without the need to overdrive the LED by illuminating an exterior surface of a phosphor layer of a white LED with UV/Violet/Blue light.

Figure 2:
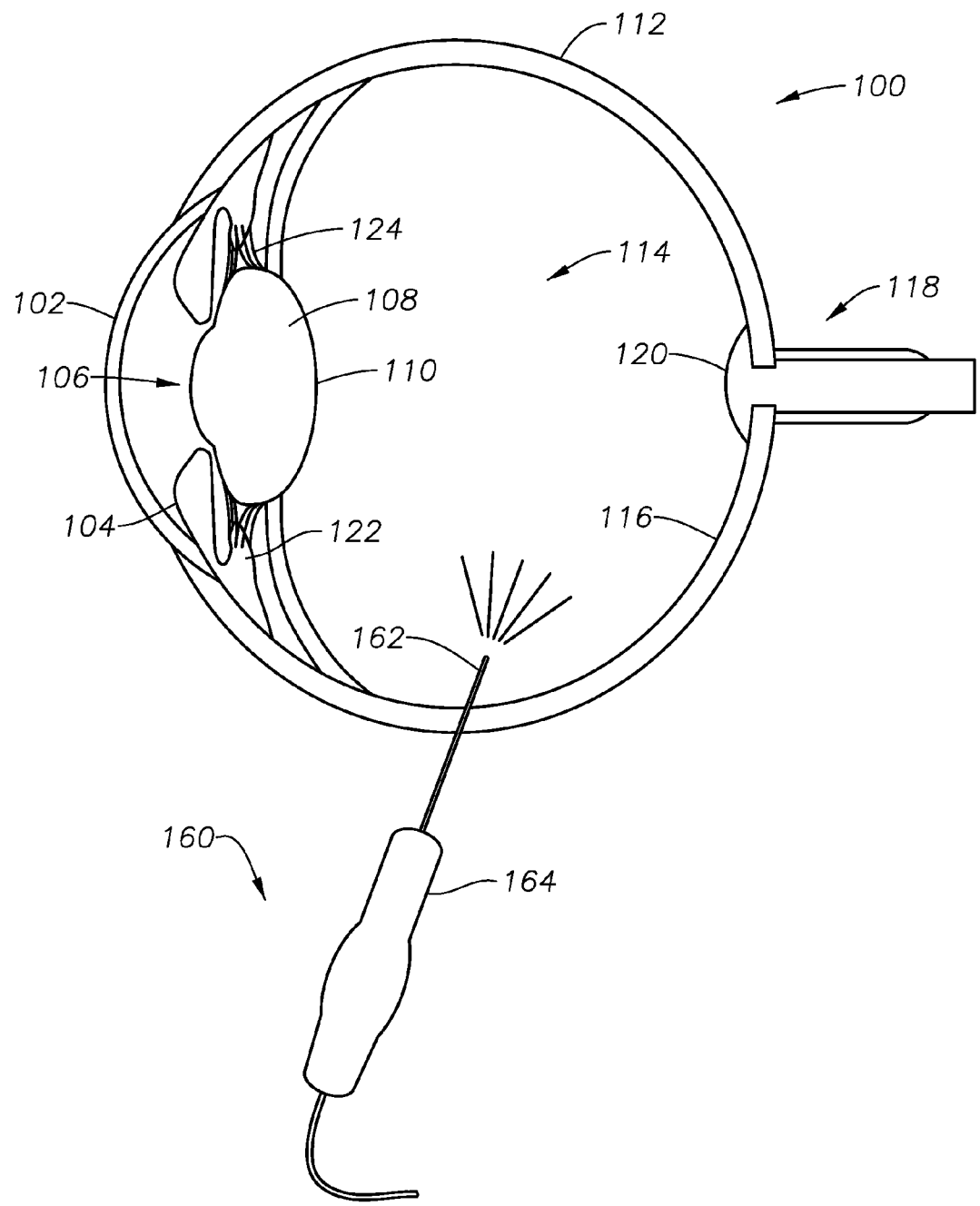
FIG. 2 illustrates an ophthalmic endoilluminator illuminating the interior of the eye in accordance with embodiments of the present disclosure.

FIG. 2 is cross section view of an ophthalmic endoilluminator 160 located in an eye according to an embodiment of the present disclosure. FIG. 2 depicts hand piece 164 and probe 162 in use. Probe 162 is inserted into eye 100 through an incision in the pars plana region. Probe 162 illuminates the inside or vitreous region 114 of eye 100. In this configuration, probe 162 can be used to illuminate the inside or vitreous region 114 during vitreo-retinal surgery.

The output of fiber coupled illuminators depends on the brightness of the light source and the coupling efficiency of the light into the fiber optic. As the physical size and/or numerical aperture of the fiber optic decreases, the brightness level of the source must increase proportionally in order to maintain the desired output through smaller fibers. This results in required source brightness levels that are higher than LEDs can provide. Hence, fiber-optic surgical illuminators in the past have relied upon high brightness sources (such as Xenon arc lamps, mercury vapor lamps, or metal halide lamps) to achieve enough light at the output of a fiber probe for surgery. White LEDs have several advantages for fiber-coupled surgical illumination applications. However, the current state-of-the-art off-the-shelf white LEDs do not provide brightness levels high enough to compete with these lamp sources without the use of brightness enhancements. Embodiments of the present disclosure describe an optical method of brightness enhancement that can push LED brightness beyond the threshold required for present day high power white LEDs to compete with lamp sources for ophthalmic illumination applications.

The simplest and most straightforward brightness enhancement for a white LED is to overdrive the LED by increasing the drive current to the LED junction beyond its rated drive current in order to achieve higher brightness. The lifetime of an LED is dependent (primarily) on two main operating parameters: operating temperatures, and current density, where increasing either or both parameters results in decreased LED lifetime. Hence, overdriving LEDs to achieve higher brightness levels, even with adequate cooling, is met with a tradeoff in LED lifetime.

Phosphor-converted white LEDs create white light by coating a blue LED die with a phosphor layer. A portion of the blue light pumps the phosphor which provides broadband fluorescence that is predominantly yellow in color. The phosphor layer thickness is tuned such that a portion of blue light transmits through the phosphor layer to create white light. LED phosphors operate in an under-saturated condition and hence, if more blue light is provided to the phosphor, be it from the underlying LED or another source, the brightness of the LED will be increased. Using a second pump source focused on the LED from the front side increases the brightness of the LED, enabling the original LED to be run at lower drive currents, thereby resulting in extended LED lifetime, while achieving the same brightness level as a single over-driven white LED.

In one example, as will be discussed with reference to FIG. 3, the output of a white LED is optically boosted, substantially collimated and directed into an optical fiber by condensing optics. The output of the white LED is produced from (1) an LED die illuminating an interior surface of a phosphor layer of the white LED within the absorption band of phosphor material of the phosphor; and (2) an external light source illuminating an exterior surface of a phosphor layer of the white LED within the absorption band of phosphor material of the phosphor. The result is increased optical output from the phosphor without the need to overdrive the LED die. The output is then easily coupled into a standard ophthalmic endoilluminator optical fiber through a ball lens or other optics. Note that the core diameter and numerical aperture may be chosen to be equal or smaller than that of the endoilluminator fiber.

Figure 3:
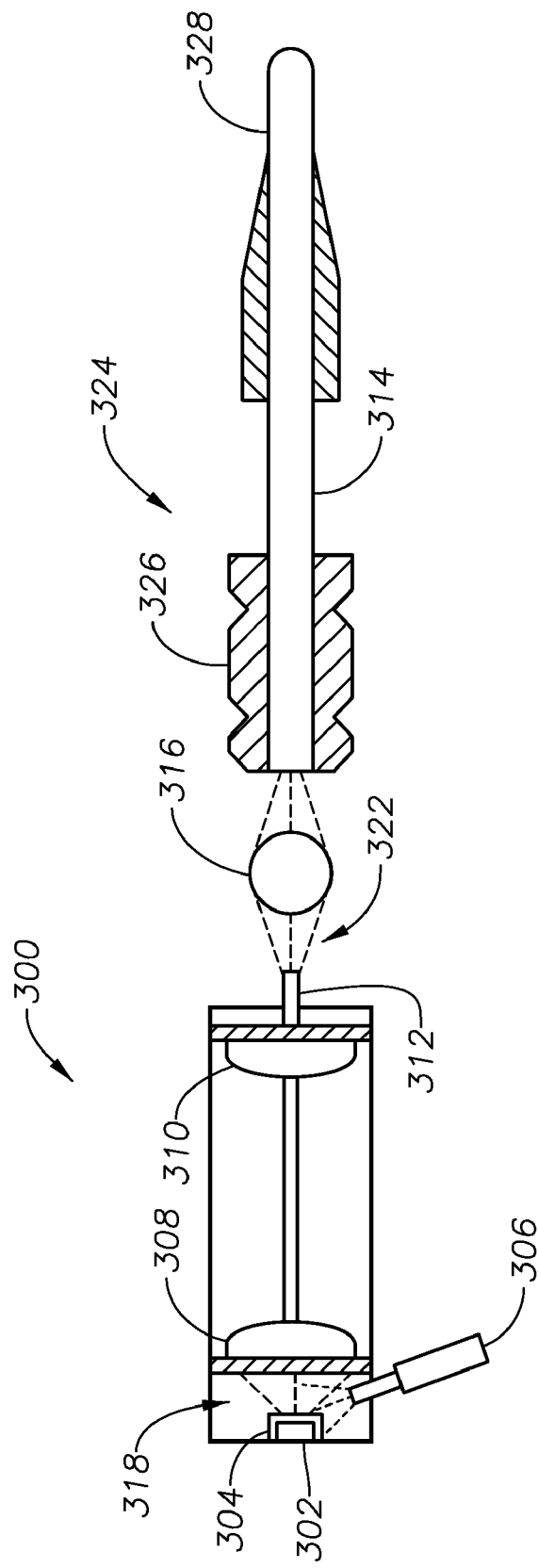
FIG. 3 is a cross-sectional diagram of a LED ophthalmic endoilluminator 300 in accordance with embodiments of the present disclosure.

FIG. 3 is a cross-sectional diagram of a LED ophthalmic endoilluminator 300 in accordance with embodiments of the present disclosure. Ophthalmic Endoilluminator 300 includes a LED 302, phosphor cap 304, secondary pump source 306 (i.e. blue or UV LED or laser, other LED, lamp source, etc), collimating optics 308, condensing optics 310 and optical fiber 312. Secondary pump source 306 irradiates the phosphor layer 304 of a white LED 302 with light within the absorption band of the phosphor material. Auxiliary pumping of the phosphor layer increases the brightness of the white LED source. Additionally, optical fiber 312 may be a scintillator fiber, in which the cladding and/or the core is luminescent. Such a fiber may be used to convert UV/Violet/Blue light illumination (pump) into broadband or white light through luminescence. Part of the re-emitted white light propagates through the scintillator fiber and can be either coupled to a regular optical fiber or directly delivered to an illumination device.

Optical fiber 312 can optically couple to an ophthalmic endoilluminator fiber 314 through a ball lens 316 or other comparable optical system. The core diameter and numerical aperture of optical fiber 312 may be chosen such that it is equal to or less than that of the optical fiber 314 within ophthalmic endoilluminator probe 324. The white light output 322 is directed through optical element 316 and optical fiber 314 to, e.g., probe 324/162 where it illuminates the inside of the eye 100. Embodiments of the present disclosure may utilize one or more LEDs to produce a constant and stable output 322. As is known, there are many types of LEDs with different power ratings and light output that can be selected as a source 302.

An optional mirror can be used as a dichroic reflector that reflects visible wavelength light and only transmits infrared and ultraviolet light to produce a beam filtered of harmful infrared and ultraviolet rays. Such a mirror reflects long wavelength infrared light and short wavelength ultraviolet light while transmitting visible light. The eye's natural lens filters the light that enters the eye. In particular, the natural lens absorbs blue and ultraviolet light which can damage the retina. Providing light of the proper range of visible light wavelengths while filtering out harmful short and long wavelengths can greatly reduce the risk of damage to the retina through aphakic hazard, blue light photochemical retinal damage and infrared heating damage, and similar light toxicity hazards. Typically, a light in the range of about 430 to 700 nanometers is preferable for reducing the risks of these hazards. Optional mirrors can be selected to allow light of a suitable wavelength to be emitted into an eye. Other filters and/or dichroic beam splitters may also be employed to produce a light in this suitable wavelength range.

The endoilluminator probe 324 that is handled by the ophthalmic surgeon includes an optical coupling 316, optical fiber 314, hand piece 326, and probe tip 328. Optical coupling 316 is designed to connect the optical fiber 314 to a main console (not shown) containing the light source 300. Optical coupling 316 properly aligns optical fiber 314 with the beam of light that is to be transmitted into the eye. Optical fiber 314 is typically a small diameter fiber that may or may not be tapered. Hand piece 326 is held by the surgeon and allows for the manipulation of probe tip 328 in the eye. Probe tip 328 is inserted into the eye and carries optical fiber 314 which can terminate at the end of probe tip 328. Probe 328 thus provides illumination from optical fiber 314 in the eye.

Embodiments of the present disclosure may also employ one or more fluorescent fibers which have been doped with red, green, and blue (RGB) organic dyes. This organic dye and UV LED pumping method is already known to those having skill in the art. For example three coils of such RGB fibers placed into an integrating sphere and illuminated with UV LEDs will create a strong RGB output. Then the individual RGB outputs may be combined onto a single fiber. This can be done in a multitude of ways, such as, but not limited to, an RGB X prism, a dispersion prism, or a diffraction grading.

Figure 4A:
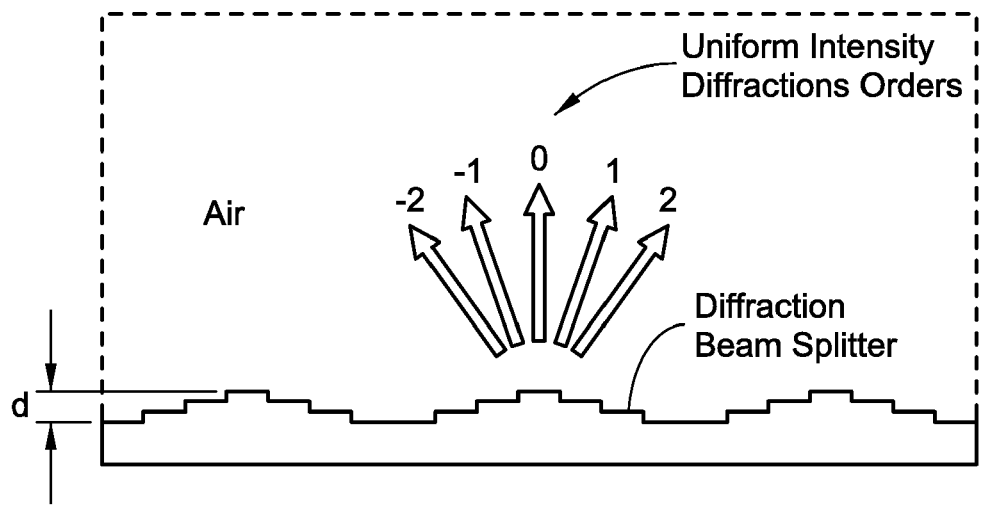
FIGS. 4A and 4B depict a standard diffraction beam splitter grating in air and saline solution.
Figure 4B:
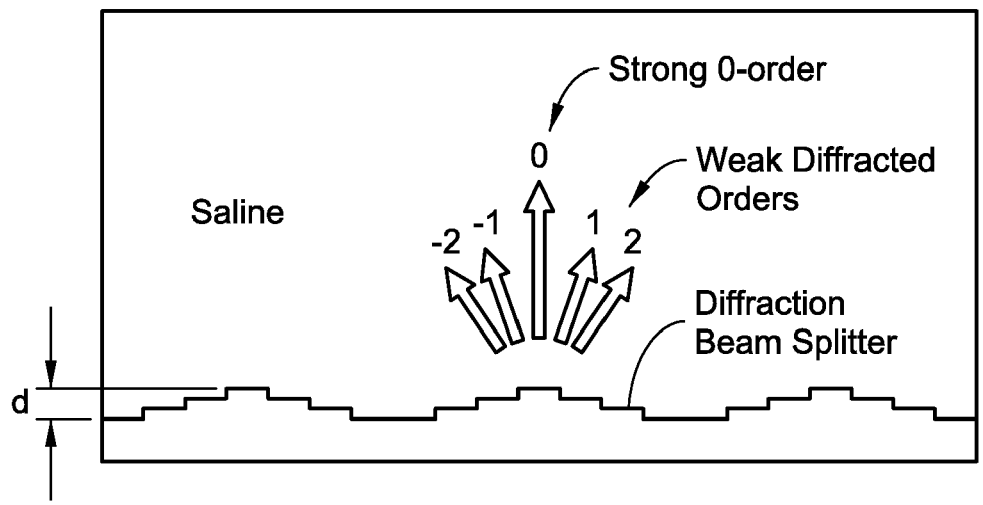

FIGS. 4A and 4B depict a standard diffraction beam splitter grating in air and saline solution. The diffraction beam splitter used in a standard single-fiber multi-spot laser probe is a surface relief grating such as that shown in FIGS. 4A and 4B. The grating is designed to strongly diffract the incident light into N diffraction orders, where the power distribution among the N orders is very uniform. This characteristic relies on the fact that the surface relief grating is immersed in air (see FIG. 4A). However, during vitreoretinal surgery, the eye is typically filled not with air but with saline solution or oil. If the grating is on the distal side of the grating substrate, then it will be immersed in liquid during vitreoretinal surgery. The result will be to severely weaken the diffraction efficiency of the grating into non-zero diffraction orders, as is illustrated in FIG. 4B.

Figure 5A:
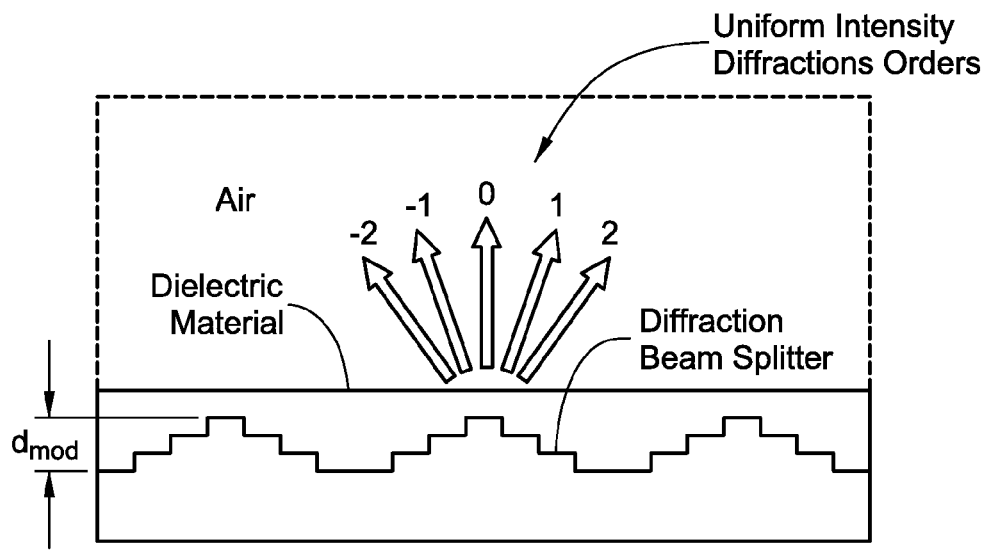
FIGS. 5A and 5B depict a diffraction beam splitter grating in accordance with embodiments of the present disclosure in air and saline solution.
Figure 5B:
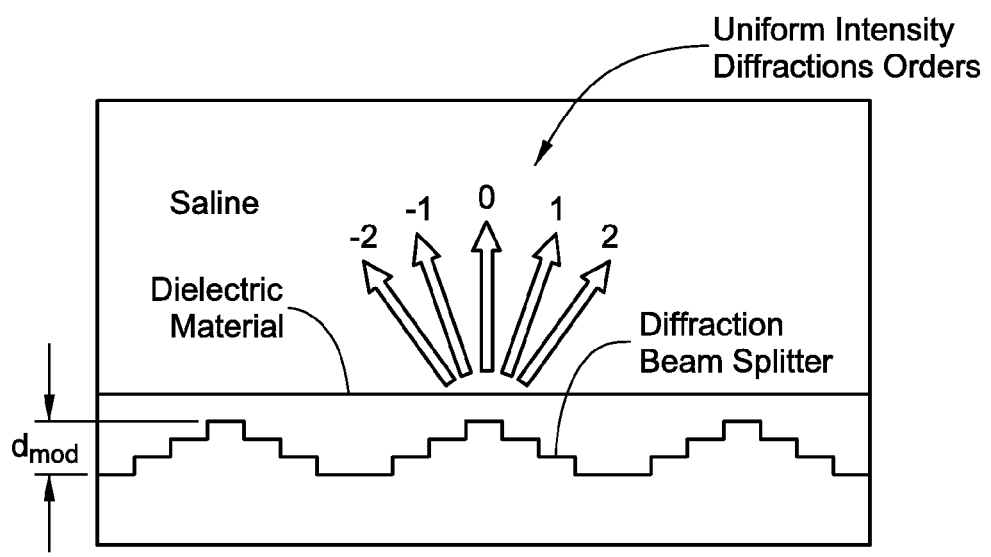

FIGS. 5A and 5B depict a diffraction beam splitter grating in accordance with embodiments of the present disclosure in air and saline solution. By making the surface relief structure thicker (see FIGS. 5A and 5B) and by filling the surface relief structure with a layer of dielectric material, the resultant grating has strong, uniform diffraction into the N diffraction orders regardless of whether the grating is immersed in air or saline solution.

Figure 6:
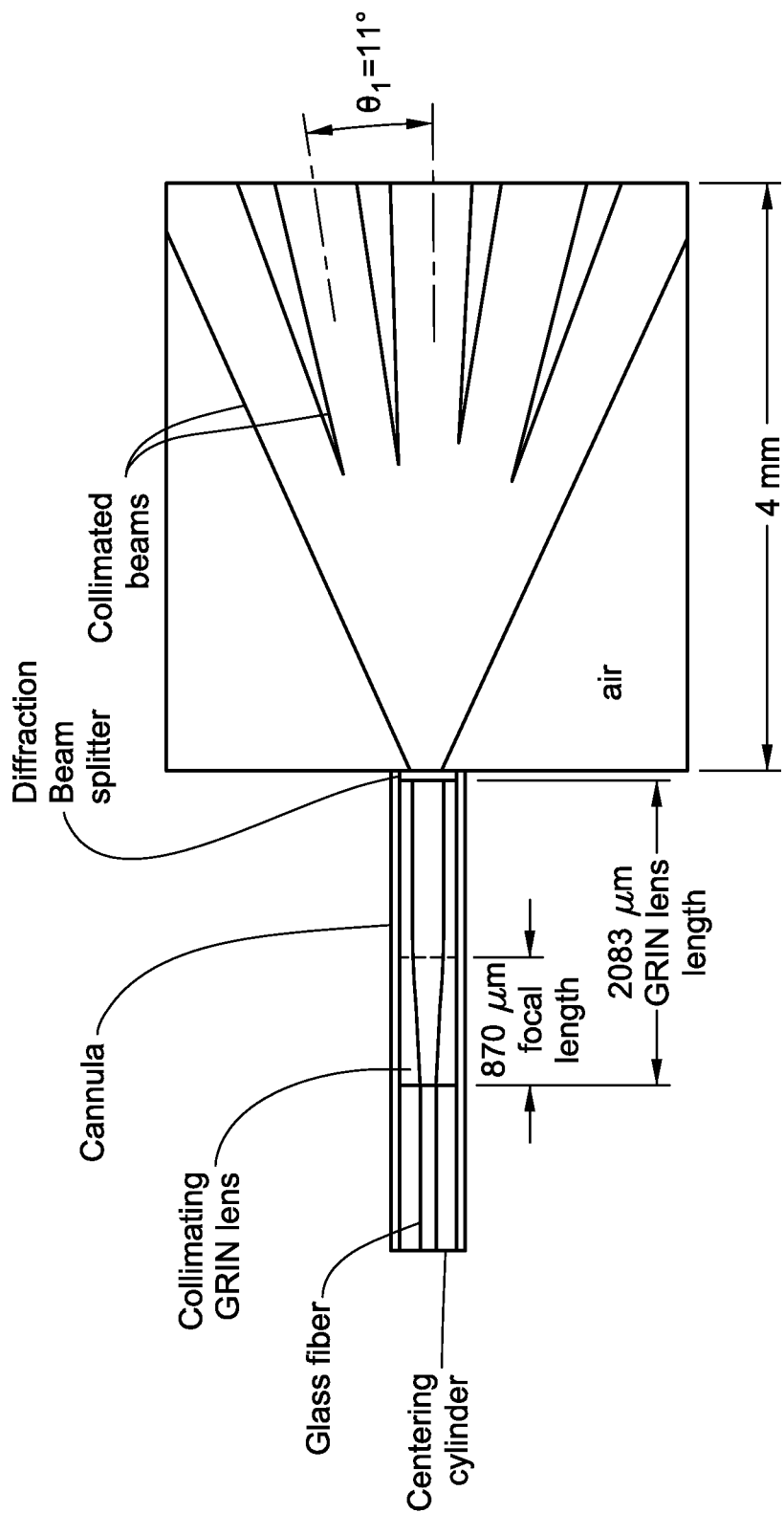
FIG. 6 depicts a prior art single-fiber multi-spot laser probe.
Figure 7A:
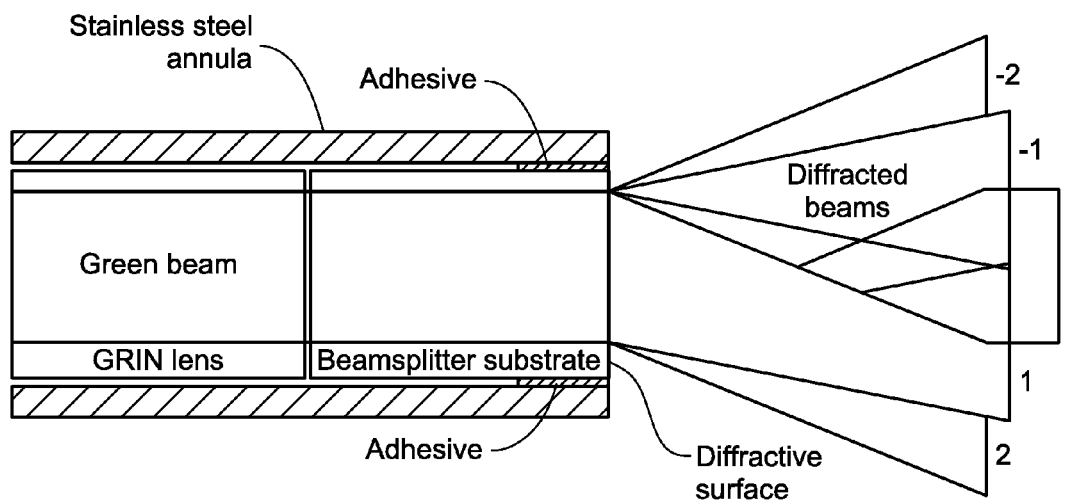
FIG. 7A depicts a diffraction beam splitter with the diffractive surface of the diffraction beam splitter substrate facing distally toward the retina.
Figure 7B:
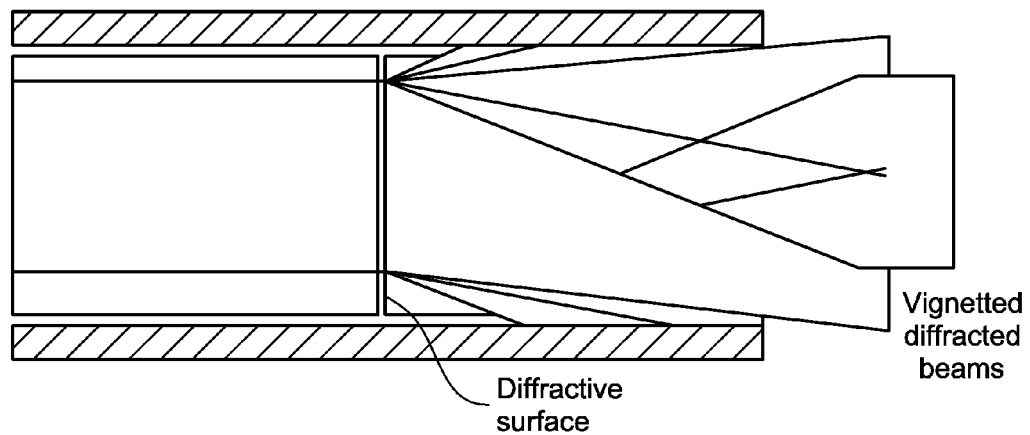
FIG. 7B depicts a diffraction beam splitter with the diffractive surface of the diffraction beam splitter substrate facing proximally toward the beam source.

A prior art single-fiber multi-spot laser probe is illustrated in FIG. 6. The diffraction beam splitter in FIG. 6 is a surface relief grating designed to be immersed in air. The standard configuration, illustrated in FIG. 7A, is to have the diffractive surface of the diffraction beam splitter substrate facing distally toward the retina. This configuration is vulnerable to immersion in saline solution during vitreoretinal surgery which will destroy the desired performance of the diffraction beam splitter. An alternative approach, illustrated in FIG. 7B, is to have the diffractive surface of the diffraction beam splitter substrate facing proximally toward the beam source. In this configuration, the grating is protected from exposure to saline solution and therefore will retain its desired diffraction efficiency properties. However, as we can see in FIG. 7B, the off-axis diffracted beams are partially vignetted by the cannula. This is a problem for several reasons:

The goal of <10% non-uniformity in diffracted beam power between the diffracted and zero order beams is not met; and The off-axis diffracted beams have less laser power than desired and therefore will require a longer exposure time in order to create the desired laser burn pattern on the retina.

Figure 8:
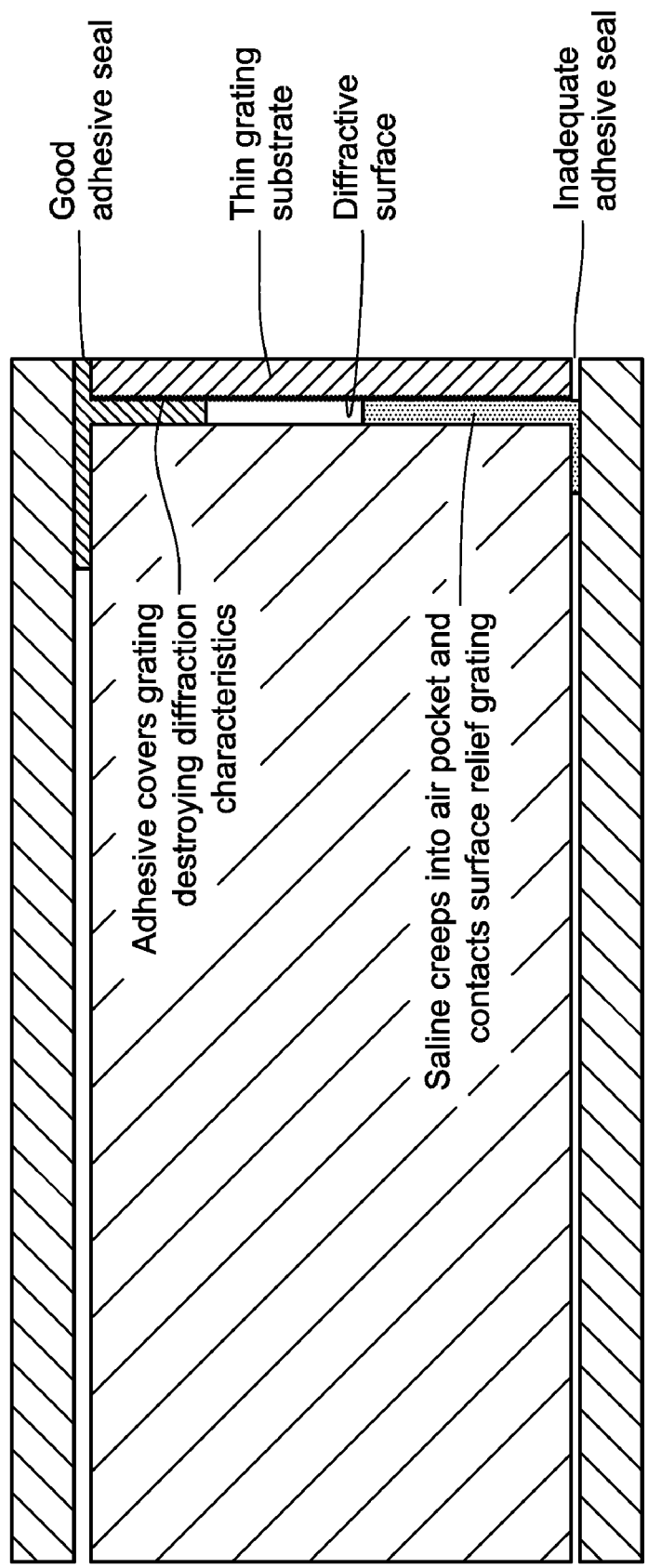
FIG. 8 depicts problems associated with having an ultra-thin diffraction grating substrate.

FIG. 8 illustrates problems associated with having an ultra-thin diffraction grating substrate. To minimize this vignetting effect, the diffraction grating substrate would need to be made as thin as possible. However, such a thin substrate would have little structural integrity and would need to be optically bonded to the GRIN lens. However, it is not desirable to bond the surface relief grating to the GRIN lens because the bonding adhesive will essentially index match with the refractive index of the GRIN lens and the diffraction beam splitter substrate, and the grating efficiency characteristics will be destroyed. The grating substrate instead would need to be secured by bonding the cylindrical side wall of the beam splitter substrate to the cannula. It is necessary that this adhesive bond totally seals the periphery of the grating substrate to the cannula to preventingress of saline solution to the air space behind the grating substrate. However, it is very difficult to avoid the adhesive from creeping over onto the diffractive grating surface, as in FIG. 8.

The modified diffraction beam splitter illustrated in FIGS. 5A and 5B has the following advantages over the prior art diffraction beam splitters used in the single-fiber, multi-spot laser probe. The surface relief grating can be on the distal side of the grating substrate, thereby avoiding the beam vignetting (and resultant problems caused by it) when the grating is on the proximal side of the grating surface. No thin grating substrate is needed since the grating can go on the distal side of the grating substrate. This avoids problems such as adhesive ingress or saline solution ingress to the back side of the grating substrate that can occur when a thin substrate is used. The grating has strong, uniform diffraction into each of N diffraction orders regardless of whether the grating is immersed in air or liquid such as saline solution or oil.

Efficient diffraction from a standard grating in FIGS. 4A and 4B relies on a large refractive index mismatch $\Delta n$ between the grating substrate material (typically—1.45-1.55) and the surrounding air (index=1). Efficient diffraction also relies on the depth d of the grating structure. To first order, the diffraction efficiency of the grating is dependent on the $\Delta n*d$ product.

Likewise, the modified grating in FIGS. 5A and 5B requires a significant refractive index mismatch $\Delta n_{mod}$ between the grating substrate material and the dielectric material into which the grating surface is immersed. It also relies on the depth d of the grating structure. To first order, the diffraction efficiency of the grating is dependent on the $\Delta n_{mod}*d_{mod}$ product. The index modulation $\Delta n_{mod}$ will typically be much small than $\Delta n$ because the refractive index of the immersing dielectric material is likely to be much higher than the index of air (~1.0) and much closer to the index of the grating substrate. To compensate, the depth of the grating features must increase proportionally, according to the formula:

$$d_{mod} = d\left(\frac{\Delta n}{\Delta n_{mod}}\right)$$

For example, if $\Delta n_{mod}=\frac{1}{3} \Delta n$, then to achieve roughly equivalent high efficiency, $d_{mod}$ must be three times deeper than d. In the modified grating, if the refractive index of immersing dielectric material is around 1.5 then to achieve significant $\Delta n_{mod}$ the grating substrate should be made out of high index glass with a refractive index much higher than 1.5.

The immersing dielectric layer in FIGS. 5A and 5B should have a planar specular distal surface to avoid distortion or aberration of the diffracted beams as they emerge from the dielectric layer into the ambient medium and head towards the retina. A practical method of creating this dielectric layer using blue or UV light curing optical adhesive is illustrated in FIG. 9.

The standard implementation of embodiments of the present disclosure would be similar to the configuration in FIG. 6, where the distally-facing diffractive surface is the grating structure in FIGS. 5A and 5B. This grating is typically created in the grating substrate by direct laser writing or e-beam writing onto a photo resist layer a grating pattern that is subsequently etched into the glass grating substrate using standard lithographic processes.

Figure 10:
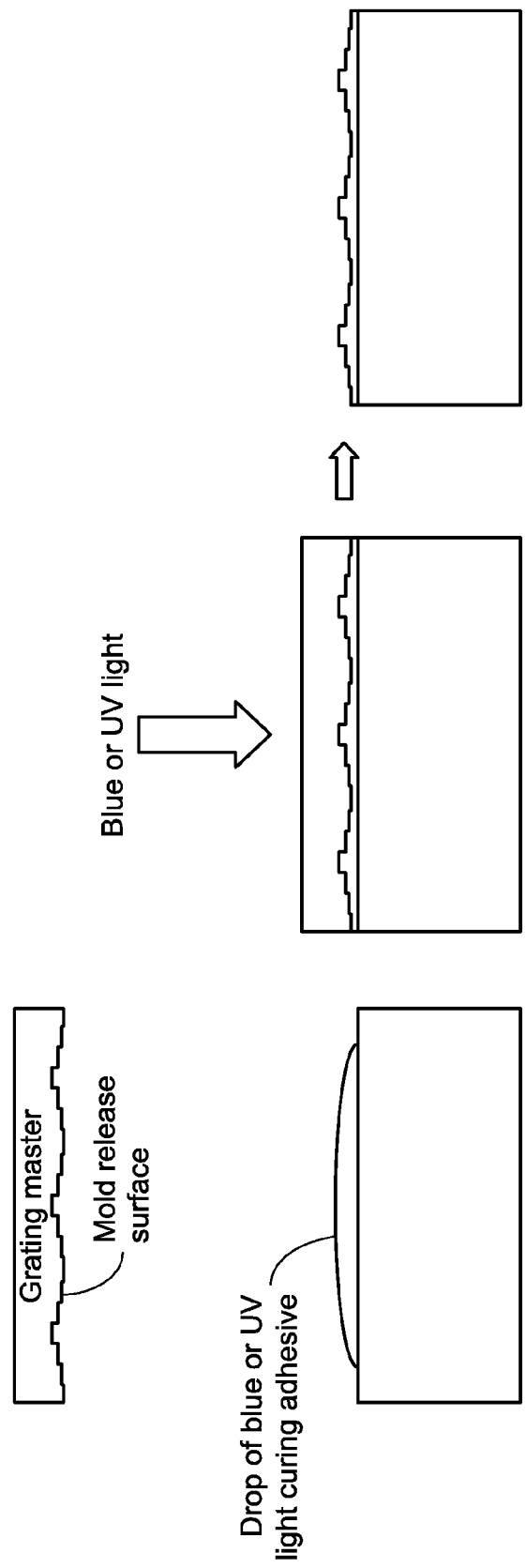

An alternative approach would be to create a grating master that is the exact inverse of the grating to be replicated, and then create a grating copy in a layer of optical adhesive, as is shown in FIG. 10.

Figure 9:
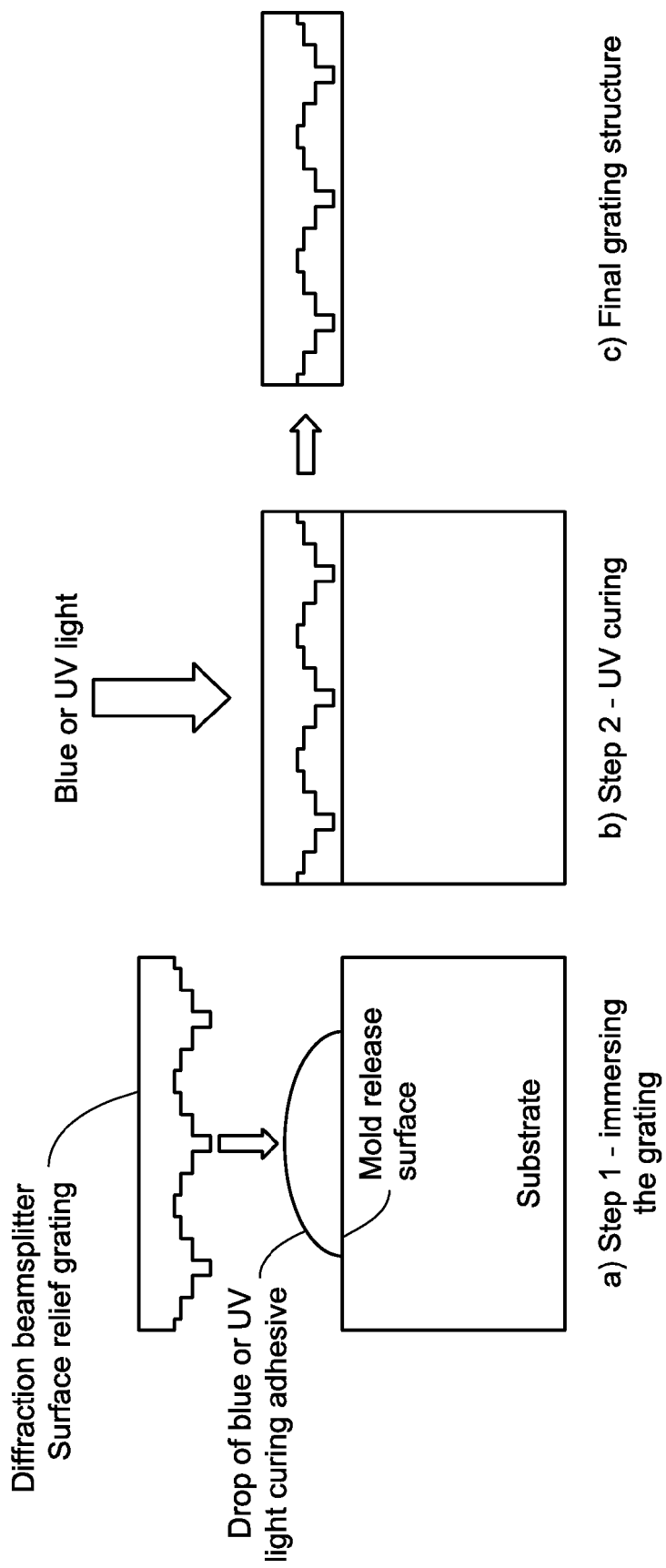
FIGS. 9 and 10 depict methods that can be combined to create the grating structure of FIG. 11 in accordance with embodiments of the present disclosure.
Figure 11:
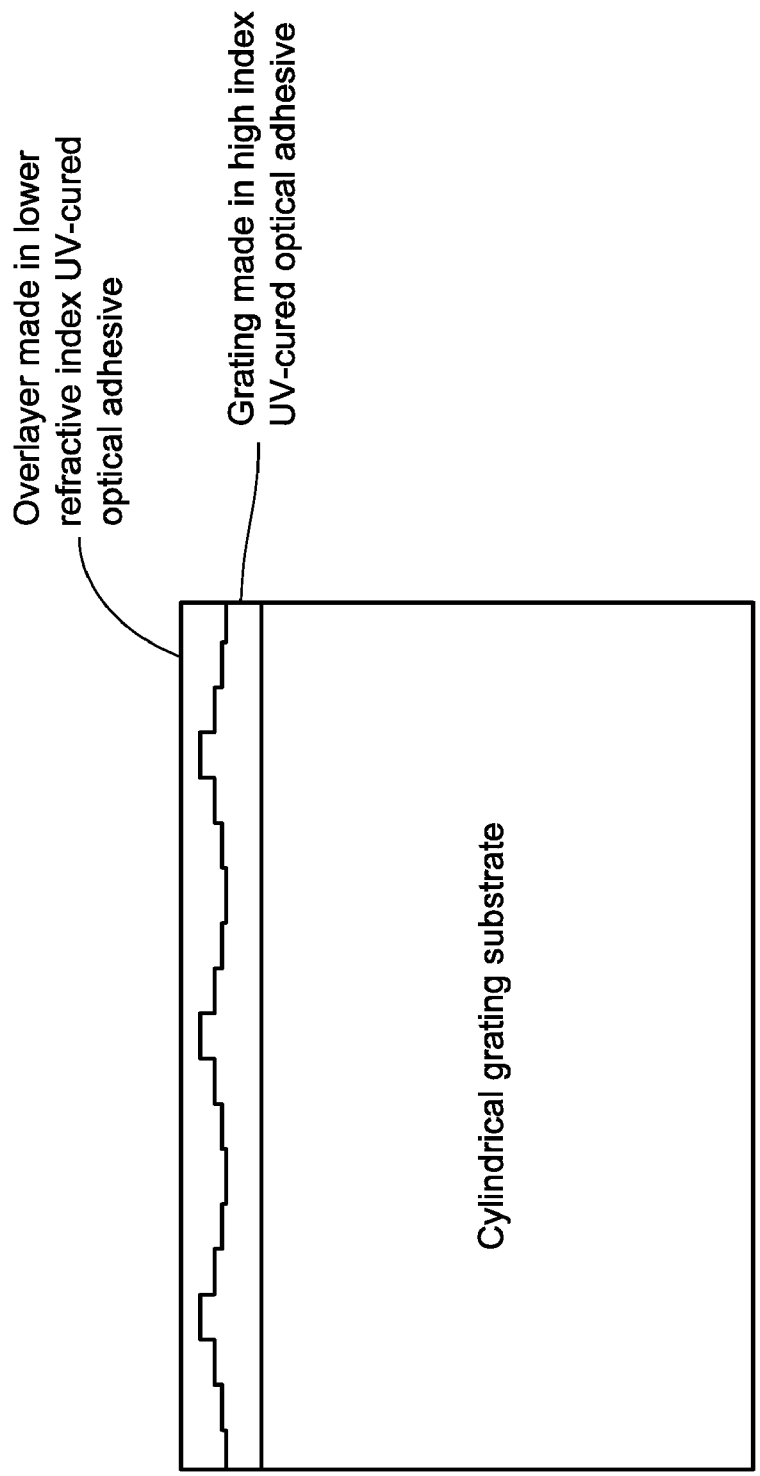
FIG. 11 depicts a grating made from high refractive index UV-cured adhesive with a dielectric overlayer made from lower refractive index UV-cured adhesive in accordance with embodiments of the present disclosure.

The methods illustrated in FIGS. 9 and 10 can be combined to create the grating structure in FIG. 11 which combines a grating made from high refractive index UV-cured adhesive with a dielectric overlayer made from lower refractive index UV-cured adhesive.

Figure 12:
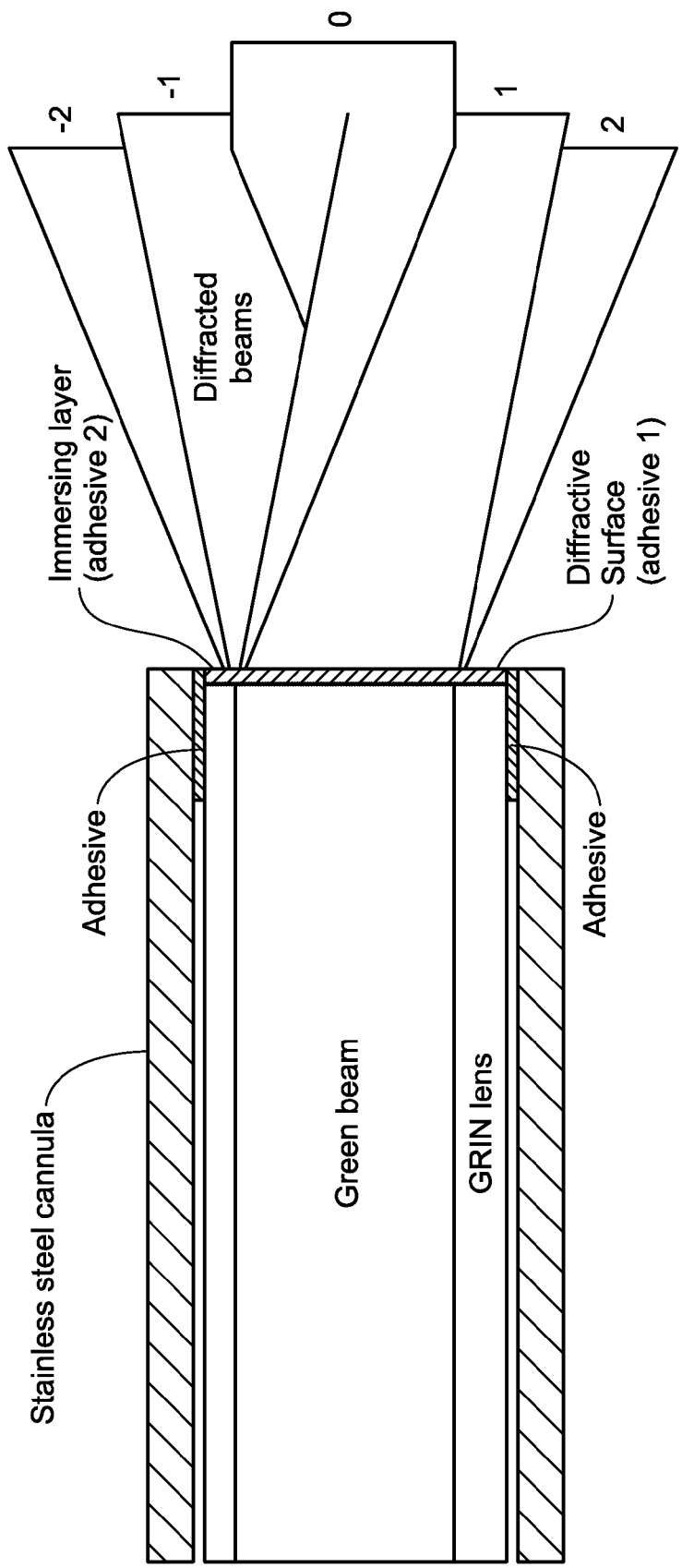
FIG. 12 depicts a two-adhesive layer grating on distal surface of GRIN lens in accordance with embodiments of the present disclosure.

FIG. 12 depicts a two-adhesive layer grating on a distal surface of a GRIN lens in accordance with embodiments of the present disclosure. It is also possible for the two-layer adhesive grating structure to be created on the distal end face of the cylindrical GRIN lens (as is illustrated in FIG. 12), thereby bypassing the need for a separate glass substrate for the grating.

Figure 13:
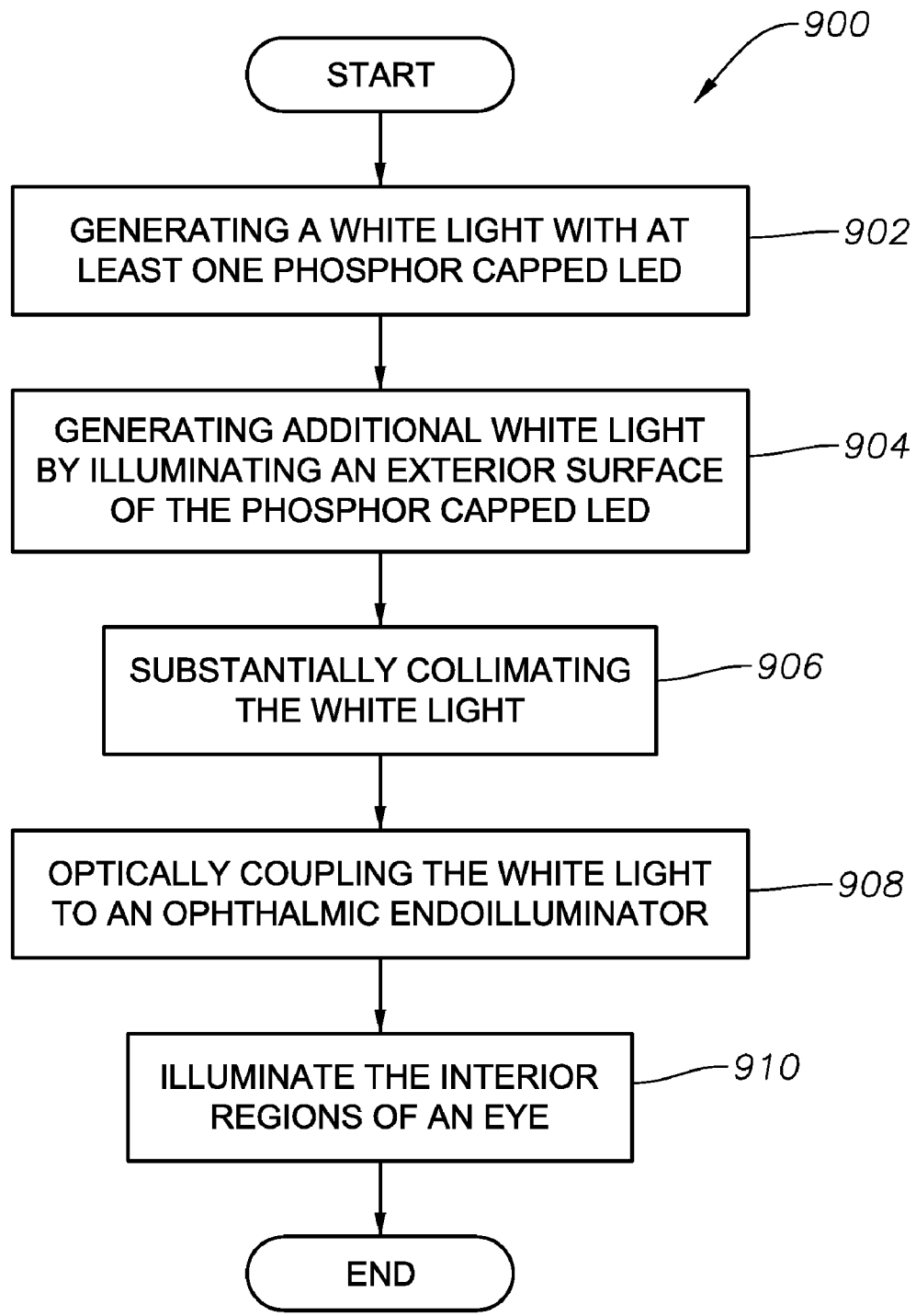
FIG. 13 provides a logic flow diagram associated with a method of illuminating the interior vitreous regions of an eye using an ophthalmic endoilluminator in accordance with embodiments of the present disclosure.

FIG. 13 provides a logic flow diagram associated with a method of illuminating the interior vitreous regions of an eye using an ophthalmic endoilluminator in accordance with embodiments of the present disclosure. Operation 900 begins with block 902 where light is generated with at least one white LED. In Block 904 additional light may be generated. The light is substantially collimated in Block 906. Block 908 optically couples this white light to an ophthalmic endoilluminator which in Block 910 may be used to illuminate the interior regions of an eye. This allows the optical fiber of the ophthalmic endoilluminator to conduct light to illuminate the interior regions of an eye in block 910.

In summary, embodiments provide an ophthalmic endoilluminator. From the above, it may be appreciated that the present disclosure provides an improved system for illuminating the inside of the eye. The ophthalmic endoilluminator includes a light source, a first optical assembly, an optical coupling element, and an optical fiber having an optical grating located distally on the optical fiber, the optical fiber optically coupled to the optical coupling element. The first optical assembly receives and substantially collimates the white light. The optical coupling element receives the substantially collimated white light from the first optical assembly and directs the light to an optical fiber. The optical grating couples to the distal end of the optical fiber, the optical grating having a surface relief grating, and an overlayer optically coupled to the surface relief grating. The optical grating is operable to substantially diffract incident light into N diffraction orders, the N diffraction orders having a substantially uniform intensity. The optical fiber/optical grating is then used to conduct the white light into an eye.

The present disclosure is illustrated herein by example, and various modifications may be made by a person of ordinary skill in the art. Although the present disclosure is described in detail, it should be understood that various changes, substitutions and alterations can be made hereto without departing from the spirit and scope of the disclosure as described.

What is claimed is:

1. An ophthalmic endoilluminator comprising:
a light source operable to produce light;
a first optical assembly coupled to the light source, the first optical assembly operable to receive and substantially collimate the light from the light source;
an optical coupling element, the optical coupling element operable to receive the substantially collimated white light from the first optical assembly;
an optical fiber optically coupled to the optical coupling element, the optical fiber operable to conduct the white light into an eye; and
an optical grating coupled to the distal end of the optical fiber, the optical grating comprising:
a surface relief grating; and
an overlayer optically coupled to the surface relief grating, the optical grating operable to substantially diffract incident light into N diffraction orders, the N diffraction orders having a substantially uniform intensity, wherein N is 2 wherein; the overlayer comprises a planar specular distal surface operable to avoid distortion or aberration of N diffraction orders beams as the beams emerge from the overlayer into an ambient medium.

2. The ophthalmic endoilluminator of claim 1, wherein: the overlayer comprises a layer of dielectric material.

3. The ophthalmic endoilluminator of claim 1, wherein: the optical grating diffracts light into the N diffraction orders having a substantially uniform intensity when the optical grating is immersed in air or saline solution.

4. The ophthalmic endoilluminator of claim 1, wherein: a refractive index mismatch exists between a refractive index of the surface relief grating and a refractive index of the overlayer.

5. The ophthalmic endoilluminator of claim 1, wherein: the refractive index of the surface relief grating is greater than that of the refractive index of the overlayer.

6. The ophthalmic endoilluminator of claim 1, wherein: an amplitude of a depth modulation of the optical grating is determined according to $$d_{mod} = d\left(\frac{\Delta n}{\Delta n_{mod}}\right)$$

where $\Delta n$ is a refractive index mismatch between a substrate of the surface grating and air, $\Delta n_{mod}$ is a refractive index mismatch between the substrate of the surface grating and the overlayer, and d is a thickness of the optical grating.

7. The ophthalmic endoilluminator of claim 1, wherein: the overlayer is created from curing optical adhesive.

8. An ophthalmic endoilluminator comprising:
a light source operable to produce light;
a first optical assembly coupled to the light source, the first optical assembly operable to receive and substantially collimate the light from the light source;
an optical coupling element, the optical coupling element operable to receive the substantially collimated white light from the first optical assembly;
an optical fiber optically coupled to the optical coupling element, the optical fiber operable to conduct the white light into an eye; and
an optical grating coupled to the distal end of the optical fiber, the optical grating comprising:
a surface relief grating; and
an overlayer optically coupled to the surface relief grating, wherein a refractive index mismatch exists between a refractive index of the surface relief grating and a refractive index of the overlayer, the optical grating operable to substantially diffract incident light into N diffraction orders, the N diffraction orders having a substantially uniform intensity when the optical grating is immersed in air or saline solution, wherein N is 2 wherein; the overlayer comprises a planar specular distal surface operable to avoid distortion or aberration of N diffraction orders beams as the beams emerge from the overlayer into an ambient medium.

9. The ophthalmic endoilluminator of claim 8, wherein the overlayer comprises a layer of dielectric material.

10. The ophthalmic endoilluminator of claim 8, wherein: the refractive index of the surface relief grating is greater than that of the refractive index of the overlayer.

11. The ophthalmic endoilluminator of claim 8, wherein:
an amplitude of a depth modulation of the optical grating is determined according to:

$$d_{mod} = d\left(\frac{\Delta n}{\Delta n_{mod}}\right)$$

where Dn is a refractive index mismatch between a substrate of the surface grating and air, $Dn_{mod}$ is a refractive index mismatch between the substrate of the surface grating and the overlayer, and d is a thickness of the optical grating.

12. The ophthalmic endoilluminator of claim 8, wherein the overlayer is created from curing optical adhesive.

13. A method comprising:
generating light with a light source;
substantially collimating the light;
optically coupling the white light to at least one optical fiber to produce at least one optical output;
optically coupling the at least one optical output to an ophthalmic endoilluminator fiber with an optical coupling element; and
conducting the optical output with the ophthalmic endoilluminator fiber to illuminate an interior region of an eye, the ophthalmic endoilluminator fiber having an optical grating coupled to the distal end of the ophthalmic endoilluminator fiber, the optical grating operable to substantially diffract incident light into N diffraction orders the N diffraction orders having a substantially uniform intensity when the optical grating is immersed in air or saline solution, wherein N is 2 the optical grating comprising: a surface relief grating; and an overlayer optically coupled to the surface relief grating, wherein: the overlayer comprises a planar specular distal surface operable to avoid distortion or aberration of N diffraction orders beams as the beams emerge from the overlayer into an ambient medium.

14. The method of claim 13, wherein a refractive index mismatch exists between a refractive index of the surface relief grating and a refractive index of the overlayer.

15. The method of claim 13, wherein:
an amplitude of a depth modulation of the optical grating is determined according to:

$$d_{mod} = d\left(\frac{\Delta n}{\Delta n_{mod}}\right)$$

where $\Delta n$ is a refractive index mismatch between a substrate of the surface grating and air, $\Delta n_{mod}$ is a refractive index mismatch between the substrate of the surface grating and the overlayer, and d is a thickness of the optical grating.

16. The method of claim 13, the overlayer comprises a layer of dielectric material.

* * * * *